(12) United States Patent
Brichant et al.

(10) Patent No.: US 10,975,031 B2
(45) Date of Patent: Apr. 13, 2021

(54) METHOD FOR PURIFYING AROMATIC AMINO ACIDS

(71) Applicant: NOVASEP PROCESS, Pompey (FR)

(72) Inventors: Damien Brichant, Sarzeau (FR); Frédéric Schab, Lyons (FR); Stanislas Baudouin, Périgny (FR); Vincent Oriez, Maisons-Laffitte (FR)

(73) Assignee: Novasep Process, Pompey (FR)

( * ) Notice: Subject to any disclaimer, the term of this patent is extended or adjusted under 35 U.S.C. 154(b) by 0 days.

(21) Appl. No.: 15/109,286

(22) PCT Filed: Jan. 7, 2014

(86) PCT No.: PCT/FR2014/050015
§ 371 (c)(1),
(2) Date: Jun. 30, 2016

(87) PCT Pub. No.: WO2015/104464
PCT Pub. Date: Jul. 16, 2015

(65) Prior Publication Data
US 2016/0326112 A1 Nov. 10, 2016

(51) Int. Cl.
*C07D 209/20* (2006.01)
*C07D 233/64* (2006.01)
*C07C 227/40* (2006.01)
*C07C 229/34* (2006.01)
*B01J 39/04* (2017.01)
*B01J 39/20* (2006.01)
*B01J 39/05* (2017.01)

(52) U.S. Cl.
CPC ........... *C07D 209/20* (2013.01); *B01J 39/05* (2017.01); *B01J 39/20* (2013.01); *C07C 227/40* (2013.01); *C07D 233/64* (2013.01)

(58) Field of Classification Search
CPC .. C07D 209/20; C07D 233/64; C07C 227/40; C07C 229/34; B01J 39/04; B01J 39/20
USPC .......................... 548/497, 504, 339.1; 560/40
See application file for complete search history.

(56) References Cited

U.S. PATENT DOCUMENTS

| | | |
|---|---|---|
| 2,985,589 A | 5/1961 | Broughton et al. |
| 3,450,712 A * | 6/1969 | Nagano ................ C07D 209/20 548/497 |
| 3,696,107 A | 10/1972 | Neuzil |
| 3,706,812 A | 12/1972 | deRosset et al. |
| 3,761,533 A | 9/1973 | Otani et al. |
| 4,036,745 A | 7/1977 | Broughton |
| 4,048,111 A | 9/1977 | Rosback et al. |
| 4,048,205 A | 9/1977 | Neuzil et al. |
| 4,049,688 A | 9/1977 | Neuzil et al. |
| 4,189,422 A | 2/1980 | Wakeford |
| 4,189,442 A | 2/1980 | Lubsen et al. |
| 4,313,015 A | 1/1982 | Broughton |
| 4,329,280 A | 5/1982 | Cleary et al. |
| 4,353,838 A | 10/1982 | Cleary et al. |
| 4,353,839 A | 10/1982 | Cleary et al. |
| 4,404,145 A | 9/1983 | Cleary et al. |
| 4,433,195 A | 2/1984 | Kulprathipanja |
| 4,460,675 A | 7/1984 | Gruetzmacher et al. |
| 4,486,618 A | 12/1984 | Kulprathipanja et al. |
| 4,495,106 A | 1/1985 | Cleary et al. |
| 4,497,710 A | 2/1985 | Wagu et al. |
| 4,511,514 A | 4/1985 | Cleary et al. |
| 4,519,952 A | 5/1985 | Cleary et al. |
| 4,521,343 A | 6/1985 | Chao et al. |
| 4,522,761 A | 6/1985 | Cleary et al. |
| 4,524,029 A | 6/1985 | Cleary et al. |
| 4,524,030 A | 6/1985 | Cleary et al. |
| 4,529,551 A | 7/1985 | Cleary et al. |
| 4,560,675 A | 12/1985 | Cleary et al. |
| 4,605,783 A | 8/1986 | Zinnen |
| 4,720,579 A | 1/1988 | Kulprathipanja |
| 4,764,276 A | 8/1988 | Berry et al. |
| 4,797,233 A | 1/1989 | Zinnen |
| 4,882,065 A | 11/1989 | Barder |
| 4,902,829 A | 2/1990 | Kulprtahipanja |
| 4,961,881 A | 10/1990 | Ou |
| 5,064,539 A | 11/1991 | Tanimura et al. |

(Continued)

FOREIGN PATENT DOCUMENTS

| | | |
|---|---|---|
| CN | 101709048 | 5/2010 |
| CN | 101709048 A * | 5/2010 |

(Continued)

OTHER PUBLICATIONS

Beebe, Janet M., et al., "Analytical-Scale High-Performance Liquid Chromatography of Omega-3 Fatty Acid Esters Derived From Fish Oils," Journal of Chromatography, vol. 468, pp. 225-233 (1989).

Beebe, Janet M., et al., "Preparative-Scale High-Performance Liquid Chromatography of Omega-3 Polyunsaturated Fatty Acid Esters Derived From Fish Oil," Journal of Chromatography, vol. 459, pp. 369-378 (1988).

Cremasco, M. A., et al.; "Experimental Purification of Paclitaxel From a Complex Mixture of Taxanes Using a Simulated Moving Bed", Brazilian Journal of Chemical Engineering, vol. 26, No. 1, Jan.-Mar. 2009, pp. 207-218.

(Continued)

*Primary Examiner* — Joseph R Kosack
*Assistant Examiner* — Sagar Patel
(74) *Attorney, Agent, or Firm* — Harness, Dickey & Pierce, PLC (57) ABSTRACT

A method for purifying an amino acid from an initial mixture is disclosed, in which the amino acid includes an aromatic ring and has an acidity constant Ka, the method including:
- a first step of putting the initial mixture into contact with a strong cation resin, at a pH greater than or equal to pKa; and
- a second elution step with an aqueous solution of eluent having a pH greater than the pH of the first step, giving the possibility of collecting a flow enriched in the amino acid.

17 Claims, 3 Drawing Sheets

(56) References Cited

U.S. PATENT DOCUMENTS

| | | | |
|---|---|---|---|
| 5,068,418 A | 11/1991 | Kulprathipanja et al. |
| 5,068,419 A | 11/1991 | Kulprathipanja et al. |
| 5,069,883 A | 12/1991 | Matonte |
| 5,093,004 A | 3/1992 | Hotier et al. |
| 5,102,553 A | 4/1992 | Kearney et al. |
| 5,114,590 A | 5/1992 | Hotier et al. |
| 5,179,219 A | 1/1993 | Priegnitz |
| 5,225,580 A | 7/1993 | Zinnen |
| 5,300,653 A * | 4/1994 | Nozaki ............ C07C 227/40 548/496 |
| 5,405,534 A | 4/1995 | Ishida et al. |
| 5,422,007 A | 6/1995 | Nicoud et al. |
| 5,502,077 A | 3/1996 | Breivik et al. |
| 5,547,580 A | 8/1996 | Tsujii et al. |
| 5,630,943 A | 5/1997 | Grill |
| 5,656,667 A | 8/1997 | Breivik et al. |
| 5,698,594 A | 12/1997 | Breivik et al. |
| 5,719,302 A | 2/1998 | Perrut et al. |
| 5,777,141 A | 7/1998 | Brunner et al. |
| 5,790,181 A | 8/1998 | Chahl et al. |
| 5,840,181 A | 11/1998 | Patton et al. |
| 5,840,944 A | 11/1998 | Furihata et al. |
| 5,917,068 A | 6/1999 | Barnicki et al. |
| 5,945,318 A | 8/1999 | Breivik et al. |
| 6,013,186 A | 1/2000 | Patton et al. |
| 6,063,284 A | 5/2000 | Grill |
| 6,096,218 A | 8/2000 | Hauck et al. |
| 6,136,198 A | 10/2000 | Adam et al. |
| 6,204,401 B1 | 3/2001 | Perrut et al. |
| 6,306,306 B1 | 10/2001 | Voigt et al. |
| 6,313,330 B1 | 11/2001 | Kiyohara et al. |
| 6,325,598 B1 | 12/2001 | Sud et al. |
| 6,325,898 B1 | 12/2001 | Blehaut et al. |
| 6,350,890 B1 | 2/2002 | Kiy et al. |
| 6,375,839 B1 | 4/2002 | Adam et al. |
| 6,384,077 B1 | 5/2002 | Peet et al. |
| 6,409,923 B1 | 6/2002 | Nicoud et al. |
| 6,413,419 B1 | 7/2002 | Adam et al. |
| 6,433,201 B2 | 8/2002 | Fujita et al. |
| 6,471,870 B1 | 10/2002 | Nicoud et al. |
| 6,518,049 B1 | 2/2003 | Haraldsson et al. |
| 6,544,413 B1 | 4/2003 | Nagamatsu et al. |
| 6,675,839 B1 | 1/2004 | Braithwaite |
| 6,712,973 B2 | 3/2004 | Adam et al. |
| 6,713,447 B2 | 3/2004 | Beaudoin et al. |
| 6,740,243 B2 | 5/2004 | Wankat |
| 6,789,502 B2 | 9/2004 | Hjaltason et al. |
| 6,863,824 B2 | 3/2005 | Hamende et al. |
| 6,979,402 B1 | 12/2005 | Sprague et al. |
| 7,063,855 B2 | 6/2006 | Hjaltason et al. |
| 7,462,643 B1 | 12/2008 | Pamparana |
| 7,479,228 B2 | 1/2009 | Schramm et al. |
| 7,491,522 B2 | 2/2009 | Haraldsson et al. |
| 7,541,480 B2 | 6/2009 | Bruzzese |
| 7,588,791 B2 | 9/2009 | Fabritius |
| 7,667,061 B2 | 2/2010 | Binder et al. |
| 7,678,930 B2 | 3/2010 | Sondbo et al. |
| 7,705,170 B2 | 4/2010 | Geier et al. |
| 7,709,236 B2 | 5/2010 | Akimoto et al. |
| 7,718,698 B2 | 5/2010 | Breivik et al. |
| 7,732,488 B2 | 6/2010 | Breivik et al. |
| 7,807,848 B2 | 10/2010 | Wang |
| 7,901,581 B2 | 3/2011 | Bryntesson et al. |
| 8,063,235 B2 | 11/2011 | Krumbholz et al. |
| 8,216,475 B2 | 7/2012 | Valery et al. |
| 8,282,831 B2 | 10/2012 | Kessler et al. |
| 8,802,880 B1 | 8/2014 | Adam et al. |
| 9,150,816 B2 | 10/2015 | Nicoud et al. |
| 9,428,711 B2 | 8/2016 | Adam et al. |
| 2001/0025112 A1 | 9/2001 | Fujita et al. |
| 2002/0011445 A1 | 1/2002 | Lehoucq et al. |
| 2002/0068833 A1 | 6/2002 | Chanteloup et al. |
| 2002/0174769 A1 | 11/2002 | Adam et al. |
| 2003/0006191 A1 | 1/2003 | Heikkila et al. |
| 2003/0216543 A1 | 11/2003 | Wang et al. |
| 2003/0222024 A1 | 12/2003 | Hamende et al. |
| 2004/0099604 A1 | 5/2004 | Hauck et al. |
| 2005/0087494 A1 | 4/2005 | Hauck et al. |
| 2005/0245405 A1 | 11/2005 | Geier et al. |
| 2006/0008667 A1 | 1/2006 | Kim et al. |
| 2006/0086667 A1 | 4/2006 | Hauck et al. |
| 2006/0124549 A1 | 6/2006 | Bailly et al. |
| 2007/0068873 A1 | 3/2007 | Oroskar et al. |
| 2007/0148315 A1 | 6/2007 | Schaap et al. |
| 2007/0158270 A1 | 7/2007 | Geier et al. |
| 2007/0181504 A1 | 8/2007 | Binder et al. |
| 2008/0234375 A1 | 9/2008 | Breivik et al. |
| 2009/0023808 A1 | 1/2009 | Raman et al. |
| 2009/0130723 A1 | 5/2009 | Murata et al. |
| 2009/0176284 A1 | 7/2009 | Furihata et al. |
| 2010/0012584 A1 | 1/2010 | Majewski et al. |
| 2010/0069492 A1 | 3/2010 | Geiringen et al. |
| 2010/0104657 A1 | 4/2010 | Sondbo et al. |
| 2010/0160435 A1 | 6/2010 | Bruzzese |
| 2010/0163490 A1 | 7/2010 | Lasalle |
| 2010/0186587 A1 | 7/2010 | Kessler et al. |
| 2010/0190220 A1 | 7/2010 | Furihata et al. |
| 2010/0197785 A1 | 8/2010 | Breivik |
| 2010/0233281 A1 | 9/2010 | Breivik et al. |
| 2010/0267829 A1 | 10/2010 | Breivik et al. |
| 2010/0331559 A1 | 12/2010 | Feist et al. |
| 2010/0331561 A1 | 12/2010 | Schaap et al. |
| 2011/0000853 A1 | 1/2011 | Valery et al. |
| 2011/0015418 A1 | 1/2011 | Krumbholz et al. |
| 2011/0030457 A1 | 2/2011 | Valery et al. |
| 2011/0091947 A1 | 4/2011 | Kim et al. |
| 2011/0139001 A1 | 6/2011 | Hilaireau et al. |
| 2011/0168632 A1 | 7/2011 | Valery et al. |
| 2012/0214966 A1 | 8/2012 | Theoleyre et al. |
| 2012/0232141 A1 | 9/2012 | Hustvedt et al. |
| 2012/0309995 A1 | 12/2012 | Arhancet et al. |
| 2012/0330043 A1 | 12/2012 | Kelliher et al. |
| 2014/0128627 A1 | 5/2014 | Kelliher et al. |

FOREIGN PATENT DOCUMENTS

| | | | |
|---|---|---|---|
| DK | 1338316 T3 | 3/2005 | |
| DK | 1128881 T3 | 10/2005 | |
| EP | 0027874 A1 | 5/1981 | |
| EP | 0200944 A2 | 11/1986 | |
| EP | 0255824 A1 | 2/1988 | |
| EP | 0292846 A2 | 11/1988 | |
| EP | 0342629 B1 | 8/1993 | |
| EP | 0697034 A1 | 2/1996 | |
| EP | 0773283 A2 | 5/1997 | |
| EP | 0981399 A1 | 3/2000 | |
| EP | 1106602 A1 * | 6/2001 | ........ B01D 15/185 |
| EP | 1128881 A1 | 9/2001 | |
| EP | 1152755 A1 | 11/2001 | |
| EP | 1157692 A1 | 11/2001 | |
| EP | 1166840 A1 | 1/2002 | |
| EP | 1250058 A1 | 10/2002 | |
| EP | 1250059 A2 | 10/2002 | |
| EP | 1392411 A1 | 3/2004 | |
| EP | 1436370 A1 | 7/2004 | |
| EP | 1523541 A1 | 4/2005 | |
| EP | 1534807 A1 | 6/2005 | |
| EP | 1685222 A1 | 8/2006 | |
| EP | 1749079 A1 | 2/2007 | |
| EP | 1982752 A1 | 10/2008 | |
| EP | 2169038 A1 | 3/2010 | |
| EP | 2173184 A1 | 4/2010 | |
| EP | 2173699 A1 | 4/2010 | |
| EP | 2295529 A2 | 3/2011 | |
| EP | 2591778 A1 | 5/2013 | |
| EP | 2801604 A1 | 11/2014 | |
| EP | 2883860 A1 | 6/2015 | |
| FR | 2103302 A5 | 4/1972 | |
| FR | 2557872 A1 | 7/1985 | |
| FR | 2651148 A1 | 3/1991 | |
| FR | 2651149 A1 | 3/1991 | |
| FR | 2785196 A1 | 5/2000 | |
| FR | 2889077 A1 | 2/2007 | |
| FR | 2897238 A1 | 8/2007 | |

(56) References Cited

FOREIGN PATENT DOCUMENTS

| | | |
|---|---|---|
| GB | 2152030 A | 7/1985 |
| GB | 2221843 A | 2/1990 |
| HK | 1078509 A1 | 6/2006 |
| JP | 5888339 A | 5/1983 |
| JP | 58109444 A | 6/1983 |
| JP | 60197209 A | 10/1985 |
| JP | 61-192797 A | 8/1986 |
| JP | S62-215564 A | 9/1987 |
| JP | H01197596 A | 8/1989 |
| JP | H04235701 A | 8/1992 |
| JP | 05168434 A | 7/1993 |
| JP | 05171177 A | 7/1993 |
| JP | 06287594 A | 10/1994 |
| JP | 08218091 A | 8/1996 |
| JP | 08512336 A | 12/1996 |
| JP | 09157684 A | 6/1997 |
| JP | H10310555 A | 11/1998 |
| JP | 11-57302 A | 3/1999 |
| JP | 11-90105 A | 4/1999 |
| JP | H11209785 A | 8/1999 |
| JP | 2001139981 A | 5/2001 |
| JP | 2010530068 A | 9/2010 |
| KR | 2002-0086721 | 11/2002 |
| SI | 1797021 T1 | 4/2009 |
| WO | WO-1987/03899 A1 | 7/1987 |
| WO | WO-94/25552 A1 | 11/1994 |
| WO | WO-98/32514 A1 | 7/1998 |
| WO | WO-98/51391 A1 | 11/1998 |
| WO | WO-99/47228 A1 | 9/1999 |
| WO | WO-00/25885 A1 | 5/2000 |
| WO | WO-00/48592 A1 | 8/2000 |
| WO | WO-01/50880 A2 | 7/2001 |
| WO | WO-01/50884 A1 | 7/2001 |
| WO | WO-01/87452 A2 | 11/2001 |
| WO | WO-01/87924 A2 | 11/2001 |
| WO | WO-2001/87451 A2 | 11/2001 |
| WO | WO-02/089946 A1 | 11/2002 |
| WO | WO-03/033631 A1 | 4/2003 |
| WO | WO-2004/007654 A1 | 1/2004 |
| WO | WO-2004/007655 A1 | 1/2004 |
| WO | WO-2005/049772 A1 | 6/2005 |
| WO | WO-2005/100519 A1 | 10/2005 |
| WO | WO-2007/012750 A2 | 2/2007 |
| WO | WO-2007/017240 A2 | 2/2007 |
| WO | WO-2007/038417 A2 | 4/2007 |
| WO | WO-2007/075499 A2 | 7/2007 |
| WO | WO-2007/093690 A1 | 8/2007 |
| WO | WO-2007/0119369 A1 | 10/2007 |
| WO | WO-2007/147554 A2 | 12/2007 |
| WO | WO-2008/004900 A1 | 1/2008 |
| WO | WO-2008/107562 A2 | 9/2008 |
| WO | WO-2008/149177 A2 | 12/2008 |
| WO | WO-2009/006317 A1 | 1/2009 |
| WO | WO-2009/014452 A1 | 1/2009 |
| WO | WO-2009/047408 A1 | 4/2009 |
| WO | WO-2009/105351 A1 | 8/2009 |
| WO | WO-2010/018423 A1 | 2/2010 |
| WO | WO-2010/119319 A1 | 10/2010 |
| WO | WO-2011/080503 A2 | 7/2011 |
| WO | WO-2013/005046 A1 | 1/2013 |
| WO | WO-2013/005047 A1 | 1/2013 |
| WO | WO-2013/005048 A1 | 1/2013 |
| WO | WO-2013/005051 A1 | 1/2013 |
| WO | WO-2013/005052 A1 | 1/2013 |
| WO | WO-2015/104464 A1 | 7/2015 |
| ZA | 8905758 A | 4/1990 |

OTHER PUBLICATIONS

Dolan, John W.; "Temperature selectivity in reversed-phase high performance liquid chromatography", Journal of Chromatography A., 965, 2002, pp. 195-205.

Guiochon, et al., "Chapter 17.8.5 Multicomponent Separations in SMB," Fundamentals of Preparative and Non-Linear Chromatography, 2nd Ed., pp. 833-835 (2006).

Heinisch, Sabine, et al.; "Sense and nonsense of high-temperature liquid chromatography", Journal of Chromatography A., 1216, 2009, pp. 642-658.

Hidajat, K., et al., "Preparative-scale liquid chromatographic separation of ω-3 fatty acids from fish oil sources," Journal of Chromatography A, vol. 702, pp. 215-221 (1995).

Hur, Jin Seok, et. al.; "New Design of Simulated Moving Bed (SMB) for Ternary Separations", Ind. Eng. Chem. Res., 44(6), 2005, pp. 1906-1913.

Keßler, Lars Christian, et al.; "Theoretical study of multicomponent continuous countercurrent chromatography based on connected 4-zone units", Journal of Chromatography A., 1126, 2006, pp. 323-337.

Kim, Jeung Kun, et al., "Designs of Simulated-Moving-Bed Cascades for Quaternary Separations," Ind. Eng. Chem. Res., vol. 43, pp. 1071-1080 (2004) (published online Jan. 20, 2004).

Krzynowek, Judith, et al.; "Purification of Omega-3 Fatty Acids From Fish Oils Using HPLC: An Overview", Proceedings of the first joint conference of the Tropical and Subtropical Fisheries Technological Society of the Americas with the Atlantic Fisheries Technological Society, 1987, pp. 74-77.

Lee, Chong Ho, et al.; "Designs of simulated moving bed systems with less than N-1 cascades", Theories and Applications of Chem. Eng., vol. 9, No. 2, 2003, pp. 1949-1952.

Lee, Kwangnam, "Two-Section Simulated Moving-Bed Process," Separation Science and Technology, vol. 35, No. 4, pp. 519-534 (2000).

Medina, A. Robles, et al., "Concentration and Purification of Stearidonic, Eicosapentaenoic, and Docosahexaenoic Acids from Cod Liver Oil and the Marine Microalga Isochrysis galbana," Journal of the American Oil Chemists' Society, vol. 72, No. 5, pp. 575-583 (1995).

Mun, Sungyong, et al.; "Optimal Design of a Size-Exclusion Tandem Simulated Moving Bed for Insulin Purification", Ind. Eng. Chem. Res., 42(9), 2003, pp. 1977-1993.

Nicolaos, Alexandre, et al.; "Application of equilibrium theory to ternary moving bed configurations (four+four, five+four, eight and nine zones): I. Linear case", Journal of Chromatography A., 908, 2001, pp. 71-86.

Nicolaos, Alexandre, et al.; "Application of the equilibrium theory to ternary moving bed configurations (4+4, 5+4, 8 and 9 zones): II. Langmuir case", Journal of Chromatography A., 908, 2001, pp. 87-109.

Nicoud, R. M.; "Chapter 13: Simulated Moving-Bed Chromatography for Biomolecules", Separation Science and Technology, vol. 2, 2000, pp. 475-509.

Nicoud, Roger M.; "Chapter 1: Simulated Moving Bed (SMB): Some Possible Applications for Biotechnology", Bioseparation and Bioprocessing: A Handbook, vol. I: Biochromatography, Membrane Separations, Modeling, Validation, 1998, pp. 1-39.

Snyder, Lloyd R., et al.; "Chapter 6: Reversed-Phase Chromatography for Neutral Samples," Introduction to Modern Liquid Chromatography, Third Edition, 2010, pp. v-xxix and 253-301.

Szepesy, L., et al.; "Continuous Liquid Chromatography", Journal of Chromatography, 108, 1975, pp. 285-297.

Wolcott, R.G., et al.; "Computer simulation for the convenient optimization of isocratic reversed-phase liquid chromatographic separations by varying temperature and mobile phase strength", Journal of Chromatography A., 869, 2000, pp. 3-25.

Xie, Yi, et al.; "Standing Wave Design and Experimental Validation of a Tandem Simulated Moving Bed Process for Insulin Purification", Biotechnology Progress, 18(6), 2002, pp. 1332-1344.

Yamamura, R., et al.: "Industrial High-Performance Liquid Chromatography Purification of Docosahexaenoic Acid Ethyl Ester and Docosapentaenoic Acid Ethyl Ester from Single-Cell Oil", Journal of the American Oil Chemists' Society, vol. 74, No. 11, Jul. 30, 1997, pp. 1435-1440, XP002166746.

Yoo, Jong Shin, et al.; "Temperature-Programmed Microcolumn Liquid Chromatography/Mass Spectrometry", J. Microcol. Sep., 4(4), Sep. 4, 1992, pp. 349-362.

Zhang, Ziyang, et al., "PowerFeed operation of simulated moving bed units: changing flow-rates during the switching interval," Journal of Chromatography A, vol. 1006, pp. 87-99 (2003).

(56) References Cited

OTHER PUBLICATIONS

Zhu, P. L., et al., "Combined use of temperature and solvent strength in reversed-phase gradient elution I. Predicting separation as a function of temperature and gradient conditions," Journal of Chromatography A, vol. 756, pp. 21-39 (1996).

Zhu, P.L., et al.; "Combined use of temperature and solvent strength in reversed-phase gradient elution: IV. Selectivity for neutral (non-ionized) samples as a function of sample type and other separation conditions", *Journal of Chromatography A.*, 756, 1996, pp. 63-72.

Zhu, Cuiru, et al.; "Elevated Temperature HPLC: Principles and Applications to Small Molecules and Biomolecules", LCGC Asia Pacific, vol. 8, No. 1, Mar. 2005, pp. 48-59.

Partial European Search Report dated Jan. 7, 2014 issued by the European Patent Office in related European App. No. 13305596.2.

Alkio, M. et al., Purification of polyunsaturated fatty acid esters from tuna oil with supercritical fluid chromatography, 2000, JAOCS, vol. 77, No. 3, pp. 315-321.

European Search Report dated May 8, 2014 issued by the European Patent Office in related European App. No. 13306701.7.

Torres C F et al; "Preparation of Purified Acylglycerols of Eicosapentaenoic Acid and Docosahexaenoic Acid and their Re-esterification with Conjugated Linoleic Acid," Enzyme and Microbial Technology, Stoneham, MA, US, vol. 32, Jan. 1, 2003 (Jan. 1, 2003), pp. 49-58.

Mitten, Jeff; Large-Scale Chromatofraphy; The Green Paradox. Novasep Process.www.guidegreen.com/uploads/final/program. May 30, 2008.

Dapremont, Olivier; Evolution of Continuous Chromatography: Moving Beyond Chiral SCPhI/ICSE Supplement: API Synthesis, Formulation Development and Manufacturing, Pharmecutical Technology, Supplement to the (Sep. 2010).

Cernak et al., Distillation—Advances from Modeling to Application—Distillation of Natural Fatty Acids and Their Chemical Derivitives. 5 pp. 109-140, Mar. 2012.

Stepanowski et al., Total Recycling of Chromatographic solvents—applied managment of methanol and acetonitrile waste. Conservation and Recycling, 35 (2002).

Observations by Third Parties on Behalf of BASF Pharma (Callanish) Ltd., Submitted to the EPO on May 19, 2015 in EP. App. No. 13305596.2 (Sent by EPO to Applicant on May 29, 2015).

International Search Report dated Sep. 26, 2014 issued by the World Intellectual Property Organization in International Application No. PCT/FR2014/050015.

Written Opinion dated Jul. 12, 2016 issued by the World Intellectual Property Organization in International Application No. PCT/FR2014/050015. English Translation provided by the World Intellectual Property Organization.

Office Action dated Mar. 27, 2020 in related Korean Patent Application No. 10-2016-7020336 with English translation.

\* cited by examiner

METHOD FOR PURIFYING AROMATIC AMINO ACIDS

CROSS-REFERENCE TO RELATED APPLICATIONS

This application is a National Phase Entry of International Patent Application No. PCT/FR2014/050015, filed on Jan. 7, 2014, which is incorporated by reference herein.

TECHNICAL FIELD

The present invention relates to a method for purifying aromatic amino acids, i.e. amino acids including an aromatic ring, and primarily tryptophan, phenylalanine, tyrosine and histidine.

BACKGROUND

Aromatic amino acids may be produced by fermentation, by enzymation or via a synthetic route. Tryptophan, phenylalanine and histidine (for infants) are part of the family of essential amino acids: as such, they are used as nutritional supplements. The amino acid must be produced via a fermentative, synthetic or enzymatic route contains impurities, among which sugars and residual substrates, minerals, pigments. These impurities have to be removed in order to attain the degree of purity required for its commercial use.

Various purification methods have been developed for purifying aromatic amino acids. They are based on the following main technologies: crystallization, liquid/liquid extraction and binding onto a resin.

Purification by crystallization is applied via an aqueous or solvent route. Pretreatment steps before crystallization are sometimes provided, so as to increase the purity of the crystals. This may be a purification step on active coal (documents CN 101245047 and CN 102146052); a membrane filtration step on a stainless steel filter (document CN 101376646); an ultrafiltration step (document CN 101691349); or a combination of several successive filtrations for removing several families of impurities, for example a microfiltration/ultrafiltration/nanofiltration sequence (document CN 01812009). Solvents are sometimes added during crystallization in order to attain better degrees of purity, such as acetic acid (documents JP 2097801 and EP 1 756 055), or an aliphatic alcohol (document EP 0 274 728). The use of these solvents causes an increase in the production costs and the costs for treating or recycling mother-liquors.

A second purification route consists of proceeding with liquid/liquid extraction of the amino acid. Thus, a purification of tryptophan was proposed, using surfactants for forming a reverse micellar phase (document CN 102382030), or using toluene (document EP 0 299 715). These techniques are never sufficient as such for attaining high degrees of purity. Pre- and post-treatment steps are necessary. Further, the application of substantial volumes of solvents is economically not very interesting for treating industrial volumes of amino acids at a scale of several kilotons/year/unit.

Finally, a third route proposes a treatment on a polymeric resin. In documents CN 101812488, CN 101948420 and US 2013/0079527, the purification is based on capturing and binding the amino acid on an adsorbent (therefore neutral) resin, and then on elution with ethanol (in the first two documents) or with a salt (in the third document).

Document FR 2 581 654 describes the adsorption of tryptophan on a weakly cross-linked strong cationic polystyrene resin. The target compound is precipitated, and then dissolved in an acid solution, notably a solution of sulfuric or hydrochloric acid having a pH from 1 to 2. The acid solution is then put into contact with a cation exchange resin, which is rinsed with water followed subsequently by elution with a base. This "batch" type method is the route currently in use today for an application to industry.

Document FR 1 502 814 describes the adsorption of tryptophan on a strong cation resin or on a strong anion resin. In both cases, the selected resin has a low cross-linking rate. In the case of strong cation resin, the pH of the mixture containing the tryptophan is adjusted to 2 before it is put into contact with the resin. Elution is carried out in two phases: first elution with a neutral saline solution for removing polluting amino acids, and then elution with a basic solution for desorbing tryptophan. This is a method requiring two distinct eluents and substantial amounts of regenerating agents.

The drawback of the above-described treatments on resins is the need for a significant consumption of concentrated chemical regenerating agent (usually 2 to 10% by mass) for eluting the amino acid after binding. An amount of effluents equivalent to that of the regenerating agent is also generated.

Document U.S. Pat. No. 5,300,653 describes the batch-wise separation on a single column of at least one aromatic amino acid from other non-aromatic amino acids on a strong cation resin of the gel type initially converted into a saline form with an alkaline metal. The solution containing the amino acid preferably has a pH from 2 to 12. The amino acid is adsorbed when the solution is passed over the resin, and then it is desorbed with water without any acid or base or organic solvent.

A drawback of this method is that the elution mode does not allow control of the ionic form of the resin. Indeed, the cation species present in the solution to be treated may be exchanged with the alkaline metal, without any eluent being able to maintain the initial ionic form. The separation performances between the amino acids may be affected by these untimely ion exchange mechanisms: therefore, the yields and purities of the produced amino acids risk decreasing or varying in an uncontrolled way over time.

The majority of these treatments on a resin is based on an application of the "batch" type, i.e. discontinuous application. The resins are installed in a column, and the successive eluents (must containing the amino acid; rinse waters; regenerated solutions—saline, basic, acid or alcoholic solutions) are successively percolated through the column.

However the aforementioned document US 2013/0079527 describes a semi-continuous separation on an adsorbent resin of the XAD7 type, in a chromatographic system with a Simulated Moving Bed (SMB) including three separation zones. The system is eluted with water or with salt. This method has the drawback of operating on an adsorbent resin, therefore a more expensive resin than ion exchange resins. Adsorbent resins also tend to be rapidly fouled. Their use requires a cleaning procedure with alcohol, with base and with acid for removing the impurities responsible for the fouling, which increases the operating constraints in terms of costs and installed equipment. Thus, there is a need for developing an improved method for purifying an aromatic amino acid, notably allowing separation between the target amino acid and impurities such as salts, sugars, colors, with a minimum consumption of chemicals.

SUMMARY

The invention first relates to a method for purifying an amino acid from an initial mixture, in which the amino acid includes an aromatic ring and has an acidity constant Ka, the method comprising:
  a first step of putting the initial mixture into contact with a strong cation resin, at a pH greater than or equal to pKa;
  a second elution step with an aqueous solution of an eluent having a pH greater than the pH of the first step, making it possible to collect a flow enriched in the amino acid.

According to an embodiment, the initial mixture further comprises sugars and/or salts, and in which the flow enriched in the amino acid includes less sugars and/or salts than the initial mixture. According to an embodiment, the second elution step is an isocratic elution step. According to an embodiment, the amino acid has a basicity constant Kb and, during the first step, the pH is less than or equal to pKb−3, preferably less than or equal to pKb−4, most preferably less than or equal to pKb−5 and ideally less than or equal to pKb−6.

According to an embodiment, the second elution step is directly carried out following the first contacting step, without any intermediate rinsing. According to an embodiment, the eluent solution is a solution of a base in water, the base preferably being soda, potash, ammonia or a mixture thereof and more preferably ammonia. According to an embodiment, the concentration of the base in the eluent solution is from 0.01 to 50 g/L, preferably from 0.2 to 20 g/L, more particularly from 0.5 to 10 g/L, and most particularly from 1 to 5 g/L.

According to an embodiment, the ratio of the number of moles of base in the eluent solution used in the second step over the number of moles of amino acid in the initial mixture put into contact in the first step is less than or equal to 3, preferably less than or equal to 2, preferably less than or equal to 1.5, preferably less than or equal to 1, preferably less than or equal to 0.9, preferably less than or equal to 0.8, preferably less than or equal to 0.7, preferably less than or equal to 0.6, preferably less than or equal to 0.5, preferably less than or equal to 0.4. According to an embodiment, the amino acid is tryptophan or phenylalanine or tyrosine or histidine. According to an embodiment, the strong cation resin is a polystyrene-divinylbenzene copolymer.

According to an embodiment, the strong cation resin has a cross-linking rate from 5 to 12%, preferably from 6 to 11%, more particularly from 7 to 10%, preferably from 8 to 9%. According to an embodiment, the strong cation resin is in a monovalent cation form, preferably in the form of $Na^+$ or $K^+$ or $NH_4^+$, and most preferably in the form of $NH_4^+$. According to an embodiment, the method is applied in a multi-column chromatographic installation, the installation including preferably at most 30 columns, more preferably at most 20 columns, or at most 12 columns, or at most 8 columns or at most 6 columns.

According to an embodiment, the method is applied in a chromatographic installation with a non-static bed, and preferably in a chromatographic installation with a simulated moving bed, or an actual moving bed, or an improved simulated moving bed, or a sequential simulated moving bed, and preferably with a sequential simulated moving bed. According to an embodiment, the initial mixture is obtained at the end of the treatment of a raw mixture, the raw mixture preferably being a fermentative, synthetic or enzymatic must, and said treatment preferably including one or several steps selected from centrifugation, front filtration, crystallization, tangential filtration, microfiltration and ultrafiltration. According to an embodiment, the method comprises one or several steps for concentrating the flow enriched in the amino acid, preferably selected from concentration by evaporation and notably by evaporation with a falling film, concentration by multi-effect evaporation, membrane concentration and notably nanofiltration.

According to an embodiment, at the end of the concentration step(s), a concentrated amino acid flow on the one hand and an eluent solution flow on the other hand are collected, the method comprising the recycling of this flow of eluent solution towards the second elution step. According to an embodiment, the difference between the pH of the eluent solution used in the second step and the pH of the first step is greater than or equal to 2, preferably greater than or equal to 4, more particularly greater than or equal to 6, and notably greater than or equal to 8.

With the present invention it is possible to overcome the drawbacks of the state of the art. It more particularly provides an improved method for purifying an aromatic amino acid, notably allowing separation between the target amino acid and impurities such as salts, sugars, colors, with a minimum consumption of chemicals. This is accomplished by the use of a strong cation resin (ion exchange resin), which is not used in an ion exchange mode. The invention is based on a chromatographic elution mode wherein the aromatic amino acid is separated from its initial solution by a delay phenomenon due to its affinity with the resin. Thus, the invention intends to put the amino acid, in majority in the zwitterionic form, into contact with the resin (pH greater than or equal to pKa of the amino acid), and then to elute it with a higher pH solution.

The operating mode differs from the existing methods which apply a capture phenomenon by immobilization of the amino acid, and then desorption with a concentrated regeneration eluent. Without intending to be bound by any theory, the inventors estimate that the separation mechanism applied is probably an adsorption phenomenon by hydrophobic interaction between the Pi bonds of the aromatic group and/or of the doublet of the nitrogen atom(s) present in the ring of the amino acid, and the hydrophobic functions of the matrix of the resin: the separation does therefore not consist in a separation by exchange of ions. The present invention may notably be applied with a diluted elution solution and with a lower eluent/amino acid ratio, which makes it possible to minimize chemical consumptions and the amounts of effluents. The invention also makes it possible to implement a purification mechanism in a controlled way, avoiding substantial variations in yield and purity of the produced amino acids.

DETAILED DESCRIPTION

The invention is now described in more detail and in a non-limiting way in the description which follows. The invention makes it possible to collect in purified form an aromatic amino acid present in an initial mixture, generally an aqueous solution (fermented, synthetic must or stemming from enzymation) containing impurities of various natures: color, salt/minerals, sugars.

Thus, according to an embodiment, the initial mixture contains sugars, for example fermentation nutrients (glucose and/or sucrose, etc.) and/or metabolites. The total sugar content (and in particular the monosaccharide and disaccharide contents) in the initial mixture may thus be for example from 0.01 to 100 g/L, and preferably from 0.1 to 15 g/L. According to an embodiment, the initial mixture contains salts, which may be mineral salts and/or organic salts. The total salt content in the initial mixture may thus be for example from 0.01 to 80 g/L, and preferably from 0.5 to 20 g/L. The conductivity of the initial mixture may for example be from 1 to 200 mS/cm, preferably from 2 to 100 mS/cm and notably from 5 to 50 mS/cm.

According to an embodiment, the initial mixture is obtained at the end of a pretreatment by clarification of the culture broth (or enzymation). This clarification operation may be conducted with various technologies:
Decantation/centrifugation.
Tangential filtration on an organic, planar or spiral membrane with a cut-off threshold typically comprised between 2,000 and 300,000 Da.
Tangential filtration on a ceramic membrane with a cut-off threshold typically greater than 10,000 Da.
Filtration on a stainless steel filter.
Combination of the preceding operations, wherein the order may be adjusted as appropriate depending on the nature of the initial mixture and on the goals of the method.

The aromatic amino acid is preferably phenylalanine, tryptophan, tyrosine, histidine or a derivative thereof. It may also be desired to recover a mixture of aromatic amino acids.

The invention provides chromatographic separation on a strong cation resin. By "strong cation resin", is meant a resin having grafted acid functions which are strong acids. According to a preferred embodiment, the "strong cation resin" means a resin including sulfonic acid functions. According to an embodiment, the cation resin is a strong polystyrene-divinylbenzene (DVB) resin.

According to an embodiment, the resin is in the form of particles, the average volume diameter (Dv50) of which is preferably from 20 to 600 μm, notably from 200 to 350 μm. Preferably, the distribution of the volume diameter of the particles of resin has only one peak (monodispersed distribution). The uniformity coefficient of this distribution may for example be less than or equal to 1.5, or less than or equal to 1.3, or less than or equal to 1.15. The resin particle size distribution may be determined by laser granulometry (NF 13320 standard).

The resin is preferably a macro-crosslinked resin (and is therefore not a resin of the gel type). Thus, according to embodiments, the crosslinking rate of the resin (DVB rate when the resin is the aforementioned copolymer) is from 5 to 6%; or from 6 to 7%; or from 7 to 8%; or from 8 to 9%; or from 9 to 10%; or from 10 to 11%; or from 11 to 12%. The crosslinking rate is defined as the ratio of the amount of crosslinking agent monomers (for example DVB monomers) over the total amount of monomers (for example DVB monomers and other monomers of the resin) which are applied in the manufacturing of the resin (the amounts being expressed in moles).

According to an embodiment, the resin is in a monovalent form. For example, it may be in the form of $Na^+$, $K^+$ or preferably $NH_4^+$. Optionally, the method of the invention may comprise a preliminary step of conditioning the resin in a desired ionic form, notably in a $Na^+$, $K^+$ or preferably $NH_4^+$ form. This preliminary step may notably be carried out by having a suitable saline or basic solution pass over the resin.

Amino acids behave like weak acids and bases. They have an acidity constant Ka and a basicity constant Kb. We define $pKa=-\log_{10}(Ka)$ and $pKb=-\log_{10}(Kb)$. The pKa and the pKb represent semi-dissociation pHs, i.e. pHs at which, the acid function, respectively the basic function of the amino acid is half ionized. The form of the amino acid in which both the acid function and the amine (basic) function are ionized is called a zwitterion.

The pKa and pKb values for the four aforementioned aromatic amino acids are the following:
Phenylalanine: pKa=1.8 and pKb=9.1.
Tryptophan: pKa=2.4 and pKb=9.4.
Tyrosine: pKa=2.2 and pKb=9.1.
Histidine: pKa=1.8 and pKb=9.2.

The invention provides a step of putting an initial mixture (or feedstock or feed product) into contact with a chromatographic resin, and then an elution step. In the first step, the pH is greater than or equal to the pKa of the desired aromatic amino acid (or the pKas of the desired aromatic amino acids, if there are several of them), in order to ensure that the amino acid is significantly in the form of a zwitterion. According to certain embodiments, the pH during the first step is greater than or equal to pKa+0.5; or greater than or equal to pKa+1; or greater than or equal to pKa+1.5; or greater than or equal to pKa+2; or greater than or equal to pKa+2.5; or greater than or equal to pKa+3. It should be noted that the pH during the first step may also be less than or equal to pKa+3; or less than or equal to pKa+2.5; or less than or equal to pKa+2; or less than or equal to pKa+1.5; or less than or equal to pKa+1; or less than or equal to pKa+0.5.

According to certain embodiments, the pH during the first step is less than or equal to pKb−3; or less than or equal to pKb−3.5; or less than or equal to pKb−4; or less than or equal to pKb−4.5; or less than or equal to pKb−5; or less than or equal to pKb−5.5; or less than or equal to pKb−6. For example, the pH during the first step may be comprised between pKa and pKb−3; or between pKa and pKb−4, or between pKa and pKb−5, or between pKa and pKb−6. According to certain embodiments, the pH during the first step is from 1.8 to 1.9; or from 1.9 to 2.0; or from 2.0 to 2.1; or from 2.1 to 2.2; or from 2.2 to 2.3; or from 2.3 to 2.4; or from 2.4 to 2.5; or from 2.5 to 2.6; or from 2.6 to 2.7; or from 2.7 to 2.8; or from 2.8 to 2.9; or from 2.9 to 3.0; or from 3.0 to 3.2; or from 3.2 to 3.4; or from 3.4 to 3.6; or from 3.6 to 3.8; or from 3.8 to 4.0; or from 4.0 to 4.5; or from 4.5 to 5.0; or from 5.0 to 5.5; or from 5.5 to 6.0; or from 6.0 to 6.5; or from 6.5 to 7.0. The pH of the feedstock (initial mixture) may be adjusted before putting it into contact with the resin by adding an acid or a base.

In the second step, the eluent is an aqueous solution having a pH greater than that of the first step. The eluent may be a basic aqueous solution, such as an $NH_3$ or NaOH solution, notably. The pH difference between the second step and the first step ($\Delta pH$) may be from 0.5 to 1.0; or from 1.0 to 1.5; or from 1.5 to 2.0; or from 2.0 to 2.5; or from 2.5 to 3.0; or from 3.0 to 3.5; or from 3.5 to 4.0; or from 4.0 to 4.5; or from 4.5 to 5.0; or from 5.0 to 5.5; or from 5.5 to 6.0; or from 6.0 to 6.5; or from 6.5 to 7.0; or from 7.0 to 7.5; or from 7.5 to 8.0; or from 8.0 to 8.5; or from 8.5 to 9.0; or from 9.0 to 9.5; or from 9.5 to 10.0; or from 10.0 to 10.5; or from 10.5 to 11.0; or from 11.0 to 11.5; or from 11.5 to 12.0. The pH of the eluent (second step) may notably be from 7.0 to 7.5; or from 7.5 to 8.0; or from 8.0 to 8.5; or from 8.5 to 9.0; or from 9.0 to 9.5; or from 9.5 to 10.0; or from 10.0 to 10.5; or from 10.5 to 11.0; or from 11.0 to 11.5; or from 11.5 to 12.0; or from 12.0 to 12.5; or from 12.5 to 13.0; or from 13.0 to 13.5; or from 13.5 to 14.0. The eluent may be a solution of a base in water, for example NaOH or $NH_3$, at a concentration from 0.001 to 0.01 g/L; or from 0.01 to 0.1 g/L; or from 0.1 to 0.5 g/L; or from 0.5 to 1 g/L; or from 1 to 2 g/L; or from 2 to 3 g/L; or from 3 to 4 g/L; or from 4 to 5 g/L; or from 5 to 6 g/L; or from 6 to 7 g/L; or from 7 to 8 g/L; or from 8 to 9 g/L; or from 9 to 10 g/L; or from 10 to 15 g/L; or from 15 to 20 g/L; or from 20 to 25 g/L; or from 25 to 50 g/L; or from 50 to 100 g/L.

According to an embodiment, the number of moles of base used for the elution, relative to the number of moles of injected amino acid is less than or equal to 3; or less than or equal to 2; or less than or equal to 1.5; or less than or equal to 1; or less than or equal to 0.9; or less than or equal to 0.8; or less than or equal to 0.7; or less than or equal to 0.6; or less than or equal to 0.5; or less than or equal to 0.4. The elution is preferably isocratic, i.e. the composition of the eluent does not vary over time.

In a preferred embodiment, the cation of the base used for the elution is the cation of the resin. Thus, for example, if the resin is in the form of $Na^+$, the eluent may be a solution of NaOH; if the resin is in the form of $K^+$, the eluent may be a solution of KOH; and if the resin is the form of $NH_4^+$, the eluent may be a solution of ammonia.

The elution by the base gives the possibility of maintaining the ionic form of the resin, which may otherwise be modified by mineral salts present in the feedstock solution. Further, without intending to be bound by any theory, the inventors assume an osmotic charge effect on the resin, which also tends to release the adsorbed species. The desired aromatic amino acid has a stronger affinity for the resin than most of the other impurities. Therefore the impurities (for example sugars and salts) are recovered in the raffinate fraction, while the amino acid is recovered in the extract.

According to an embodiment, the total mass content of sugars (in particular monosaccharides and disaccharides) in the extract is reduced by at least 80%, preferably by at least 90%, or by at least 95%, or by at least 98%, or by at least 99%, or by at least 99.5%, or by at least 99.9%, based on the total salt mass content in the initial mixture. Preferably, the extract (flow enriched in the amino acid) is without or essentially without any sugars (in particular monosaccharides and disaccharides). According to an embodiment, the total salt mass content in the extract is reduced by at least 80%, preferably by at least 90%, or by at least 95%, or by at least 98%, or by at least 99%, or by at least 99.5%, or by at least 99.9%, based on the total salt mass content in the initial mixture. Preferably, the extract (flow enriched in the amino acid) is without or essentially without any salts.

According to an embodiment, certain highly retained impurities may be desorbed by additional elution with an aqueous, saline or polar eluent. According to an embodiment, no intermediate rinsing is provided between the contacting step and the elution step. The injection of the eluent thus directly follows the injection of the initial mixture.

According to an embodiment, the recovered amino acid in the extract stemming from the chromatographic separation undergoes additional treatments, such as:

Decolorization on coal.

Demineralization.

Concentration on a membrane of the reverse osmosis type or nanofiltration.

Evaporation or multi-effect evaporation, which allows optimization of the energy consumptions.

Crystallization.

Combination of the preceding operations. The order may be adjusted as appropriate depending on the nature of the initial mixture and on the goals of the method.

According to a preferred embodiment, the eluent (preferably an $NH_3$ solution) is separated from the amino acid and recovered during the aforementioned post-treatment steps, in order to be recycled at the head of the chromatographic separation process. The method according to the invention may be discontinuous ("batch method"), semi-continuous or continuous. Preferably, it is semi-continuous or continuous.

The chromatographic separation according to the invention may be applied in a chromatographic unit with a static bed or preferably in a chromatographic unit with a non-static bed. In a chromatographic system with a static bed, the mixture of compounds to be separated percolates in a generally cylindrical enclosure (or column). The column contains a bed of porous material (stationary phase) which is permeable to fluids. The percolation rate of each compound in the mixture depends on the physical properties of the compound. The most retained compounds on the stationary phase percolate more slowly than the less retained compounds on the stationary phase. This principle gives the possibility of carrying out the desired separation.

It is possible to carry out such a treatment in several columns in series or in parallel, but generally a chromatographic separation system with a static bed is applied with a single column. Examples of such chromatographic systems with a static bed are the HPLC (High Performance Liquid Chromatography) or CYCLOJET™ (a system with recycling in the stationary state) systems.

The CYCLOJET™ system is as described in document U.S. Pat. No. 6,063,284, to which reference is expressly made. This is a discontinuous chromatographic separation system with a single column, in which the most retained species (i) and then the less retained species (ii) are collected separately at the outlet of the column, the non-separated portion of the chromatogram being recycled by the main pump, and the mixture to be separated being periodically injected by means of an injection loop essentially located in the middle of the recycled portion of the chromatogram. After several chromatographic cycles, the process reaches a periodical stationary state in which the amount of injected products is equal to the amount of separated products collected separately at the outlet of the column. An alternative of the CYCLOJET™ system using two columns is described in document U.S. Pat. No. 5,630,943, to which reference is expressly made.

A system with a non-static bed is a multi-column system, in which the relative positions of the stationary phase bed and of the injection or collecting points of the flows move over time. Examples of such chromatographic systems with a non-static bed are the SMB (simulated moving bed), iSMB (improved simulated moving bed), SSMB (sequential simulated moving bed), AMB (actual moving bed), VARICOL™, MODICON™, POWERFEED™, MCSGP or GSSR (multi-column gradient chromatography) systems.

An SMB system comprises a plurality of individual columns containing an adsorbent, which are connected in series. An eluent flow crosses the columns along a first direction. The injection points of the feed flow and of the eluent flow, as well as the points for collecting the separated compounds, are periodically and simultaneously shifted by means of a set of valves. The global effect is to simulate the operation of a single column containing a moving bed of solid adsorbent, the solid adsorbent moving in a counter-current direction relatively to the eluent flow. Thus, an SMB system consists of columns which contain stationary beds of solid adsorbent through which the eluent passes, but the operation is such that a continuous moving bed at a counter-current is simulated.

The most conventional form of an SMB system is the SMB system with four zones. Other possible forms are the SMB systems with three zones and the SMB systems with two zones (as described in the article "Two Section Simulated Moving Bed Process" of Kwangnam Lee, in Separation Science and Technology 35(4):519-534, 2000, to which reference is expressly made).

In the iSMB and SSMB systems, there is at least one step in which the system operates in a closed loop, without any product entry or exit. An iSMB system is as described in documents EP 0 342 629 and U.S. Pat. No. 5,064,539, to which reference is expressly made. An SSMB system divides the introductions and collections of the flows into subsequences applied periodically.

Other alternatives of the SMB systems are: the SMB system varying over time and the POWERFEED™ system, as described in document U.S. Pat. No. 5,102,553 and in the article "PowerFeed operation of simulated moving bed units: changing flow-rates during the switching interval", of Zhang et al. in Journal of Chromatography A, 1006:87-99, 2003, to which reference is expressly made; the MODICON™ system as described in document U.S. Pat. No. 7,479,228, to which is reference is expressly made; and the SMB system with internal recirculation, as described in document U.S. Pat. No. 8,282,831, to which reference is expressly made.

An AMB system has an operation similar to an SMB system. However, instead of displacing the feed flow and eluent injection points, as well as the collecting points, by means of a set of valves, a set of adsorption units (columns) are physically displaced relatively to the feed and collecting points. Again, the operation allows simulation of a continuous counter-current moving bed.

A VARICOL™ chromatography system is as described in documents U.S. Pat. Nos. 6,136,198, 6,375,839 6,413,419 and 6,712,973, to which reference is expressly made. A VARICOL™ system comprises a plurality of individual columns containing an adsorbent, which are connected in series. An eluent is passed into the columns along a first direction. Unlike the SMB system, the injection points for the mixture to be separated and for the eluent and the points for collecting the separated compounds in the system are periodically displaced asynchronously, by means of a set of valves. The global effect is to generate separation zones with a variable length over time, thereby allocating the stationary phase dynamically in the zones where it is the most useful, and allowing a similar power of separation with less chromatographic separation units and increased productivity. Unlike an SMB system, a VARICOL™ system does not simulate the operation of a single column containing a moving bed of solid adsorbent, the solid adsorbent moving in a counter-current direction relatively to the eluent flow, and thus the operating principle of the VARICOL™ cannot be applied in an equivalent AMB system.

Figure 1:
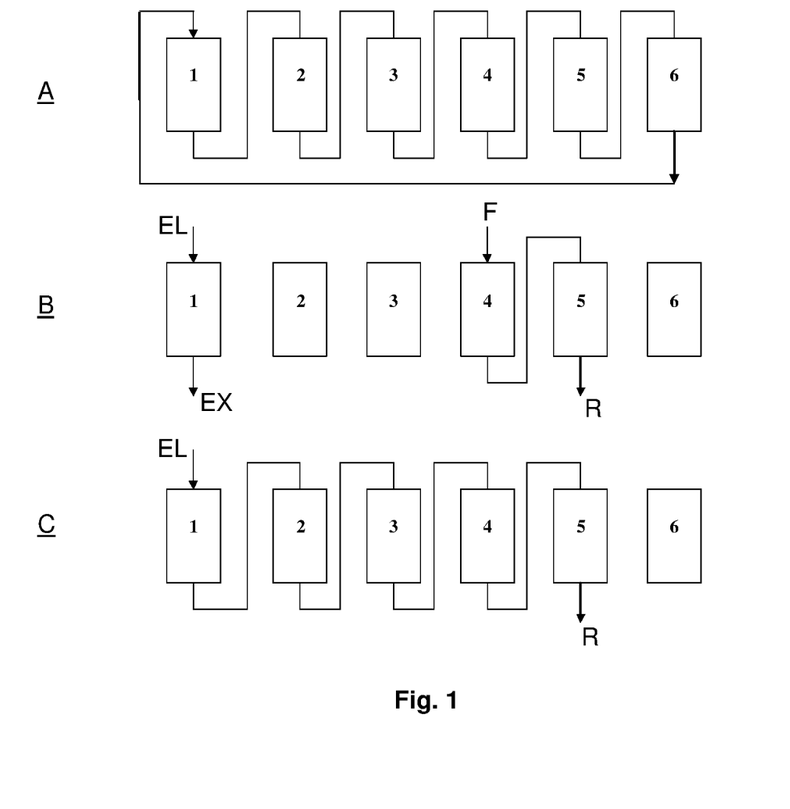
FIG. 1 schematically illustrates an installation allowing implementation of the method according to the invention.

A preferred example of a simulated moving bed is illustrated with reference to FIG. 1, in the form of a chromatography system of the sequential simulated moving bed type (SSMB) on six cells or columns. This system may be operated according to a cyclic operation in four phases.

Phase No. 1 (portion A of the figure): a loop phase during which continuous circulation in a closed loop is maintained on all the cells placed in series, for displacing the interstitial volume of one cell to the next, without injecting any eluent.

Phase No. 2 (portion B of the figure): feedstock/feedstock injection. The feedstock (F) is injected at the head of the fourth cell. Simultaneously, a substantially identical volume of raffinate (R) is collected at the outlet of the fifth cell. The cells 4 and 5 form the zone 3 here. The cells 2 and 3 form the separation zone between extract and feedstock injection. They form the zone 2 here.

Phase No. 3 (portion B of the figure): elution of the extract. The eluent (EL) is injected on the first cell for eluting the extract (EX), which is collected in a substantially identical volume at the bottom of the first cell. Cell No. 1 forms the zone 1 here.

The phases Nos. 2 and 3 are preferably operated simultaneously for increasing the productivity of the system.

Phase No. 4: elution of the raffinate. The eluent (EL) is injected at the head of the first cell and the raffinate (R) is collected in a substantially identical volume at the outlet of the fifth cell. Cell No. 6 is here a buffer cell giving the possibility of ensuring separation between the tail of the extract and the head of the raffinate. It forms the zone 4. This zone may be omitted in the case when the degree of purity and/or the desired yield is relatively limited.

These phases are operated in this order in a preferred embodiment, from 1 to 4. Their sequence forms a complete sequence. Each sequence (phases Nos. 1 to 4) is repeated six times by shifting the inlets and outlets of cells by incrementing the cell number, from left to right, of the system: the feedstock is thus injected at the top of cell No. 1 in sequence No. 1 and then at the top of cell No. 2 in sequence No. 2, etc. A complete production cycle is achieved after completing the six successive sequences, when the injection point of the feedstock, initially at the inlet of cell No. 1, returns again to the inlet of cell No. 1.

In the foregoing, a description of the SSMB system was given with reference to the case when the cells correspond to columns. This is not a limitation, and the invention also applies to systems in which the cells, or further compartments, are column portions. Moreover, the number of columns present in zones 1, 2, 3 and 4 may vary depending on the desired separation quality. It is therefore possible to devise systems of the same type with one cell, two cells, three cells, four cells and up to twelve cells or more.

The method may further be applied in a non-continuous multi-column installation with either a closed loop or an open loop, like the DCC system described in patent WO 2007/012750. According to an embodiment, a multi-column installation (notably of the SMB type or the like) contains one or several cleaning zones allowing disconnection of a column of the separation loop, in order to periodically desorb compounds (impurities) which are strongly adsorbed, and then regeneration and rebalance of the adsorbent with the eluent of the separation.

EXAMPLES

The following examples illustrate the invention without limiting it.

Example 1

Study of the Retention of Tryptophan

In this example, a tryptophan fermentation must is treated, after pretreatment by adjustment to a pH=2.6, and then microfiltration and diafiltration on ceramic membranes. The product is treated on an Applexion® XA2014-22 resin on a 30 mL volume per column (in this example, 30 mL represent 1 BV wherein BV means the Bed Volume of resin). The resin is a strong cation resin of the polymeric polystyrene-DVB type with 8% of DVB, with a monodisperse grain size of 220 μm, and with an ion exchange capability of 1.8 equiv./$L_{resin}$. The resin is converted beforehand into the Na form by means of a 4% soda solution.

The initial mixture for the chromatography step contains 17.5 g/L of tryptophan, 3.7 g/L of residual sugars, and has a conductivity of 18.5 mS/cm induced by the salts in solution. This mixture is injected in excess on the resin. During the injection phase, a behavior difference of the different species on the resin is observed:

- The saline impurities are not retained on the resin: it is estimated that an ion exclusion phenomenon between their ionic charge and the charges of the resin prevents their penetration within the matrix. Conductivity identical with that of the initial mixture is measured at the column outlet during the elution phase.
- The sugars, neutral species, may penetrate into the matrix of the resin and are slightly slowed down but not retained: they are co-eluted with the salts during the injection phase.
- The tryptophan injected in majority in the zwitterionic form at pH=2.6, as for it, undergoes a delay phenomenon by interaction between its aromatic group and those of the resin.

The elution of the thereby retained tryptophan is obtained with a soda concentration of 4 g/L, at 2 BV/h.

Figure 2:
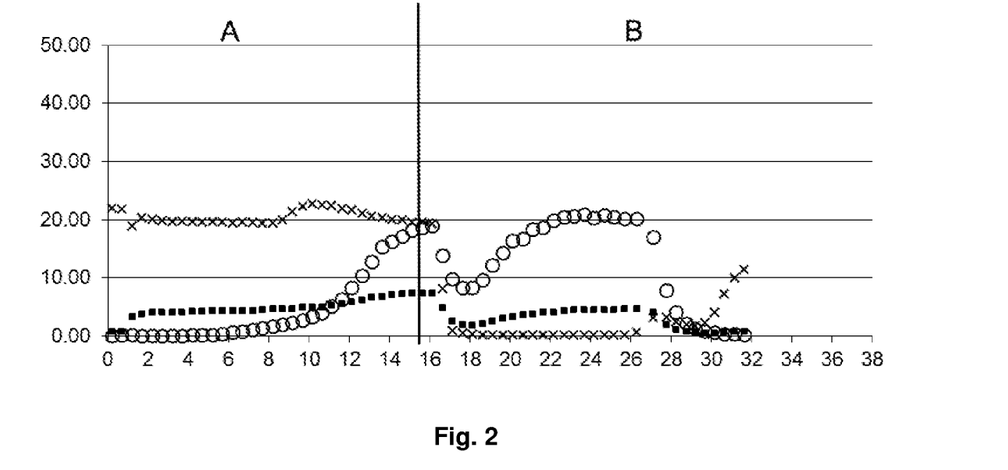
FIG. 2 illustrates the time-dependent change in the tryptophan concentration (in g/L, symbol O), in conductivity (in mS/cm, symbol X) and in dry matter amount (in Brix degrees symbol ■) according to the injected volume (in abscissa, in BV or "Bed Volumes", i.e. in multiples of the bed volume) in a chromatographic separation column. The operating conditions are specified in Example 1.

FIG. 2 illustrates the time-dependent change of the concentrations in a point of the system where the whole course of the separation steps is seen from the beginning of the elution of the raffinate to the end of the rinsing of the extract. Phase A is the injection phase of the initial mixture, phase B is the elution phase with the soda solution. This system makes it possible to operate with the following performances:

- 205.6 g of tryptophan treated per liter of resin over a production cycle of 8 hours;
- concentration <100 μS/cm during the collection of the tryptophan extract, corresponding to 99.5% of demineralization.

Example 2

Multi-Column Separation of Tryptophan

In this example, the invention is applied in a chromatographic mode on a continuous and multi-column system, to a fermentation must at pH=4 containing 40 g/L tryptophan. The main impurities are residues of substrates, minerals, as well as solid residues of cell metabolism.

The pH of the must is adjusted here to 2.7 by adding $H_2SO_4$. At this pH greater than the pKa, tryptophan is found in majority in a zwitterionic form. It is then clarified by tangential microfiltration on a ceramic membrane. The solid suspended materials are retained by the membrane and concentrated in a fraction called a retentate. Tryptophan as well as a majority of the soluble impurities are, as for them, transported through the membrane towards a fraction called a permeate. At the end of the concentration, by adding water into the retentate compartment, it is possible to dilute and then to reconcentrate the retentate: this operation, called diafiltration, allows an increase in the global yield of tryptophan by reducing its residual content in the retentate compartment.

The thereby treated microfiltration permeate contains 98% of the tryptophan initially present in the must, at a concentration of 15 g/L. The impurities are present therein in an amount of 25 g/L of mineral salts: its conductivity has the value 15.9 mS/cm. A sugar level of 3 g/L is also measured. This permeate is used as a product for feeding the SSMB system described above.

According to the SSMB principle discussed earlier, the system used in this specific case consists of 9 separation cells applied as columns and distributed as follows:

Zone 1: three columns=tryptophan elution zone;
Zone 2: two columns=separation zone;
Zone 3: three columns=slowing-down zone of the tryptophan;
Zone 4: one column=loop zone.

Each column contains 475 mL of Applexion® XA2014-22 resin. The size of a bed volume is thereby defined: 1 BV=475 mL. The resin is initially conditioned in the $NH_4^+$ form by percolation of ammonia $NH_3$ at a concentration of 3 N. The system is operated at 4.5 BV/h.

The feedstock product is injected at the head of zone 3. At each production period, 7.5 BV of feed stock product are injected. On three columns, the tryptophan is slowed down by a delay phenomenon on the resin, and thus separated from the impurities which are eluted and collected, at the outlet of the zone, in a fraction said to be a "raffinate". The majority of the impurities (salts and sugars) are eluted in this raffinate: its conductivity has a value of 17.6 mS/cm. The system is adjusted so that 0.1% of the initial tryptophan is eluted in the raffinate fraction.

At the head of zone 1, ammonia diluted to 2 g/L (eluent) is injected, which allows desorption of the tryptophan. At each production period, 5 BV of eluent are injected. The tryptophan is recovered during this elution in a so-called <<extract>> fraction. The conductivity of the extract is less than 200 μS/cm: the latter is demineralized in an amount of 98.8% relatively to the feedstock product. 89% reduction of the residual sugars and 75% of the color are also measured.

A very small amount of ammonia eluent is used: the eluent/feedstock product ratio has the value of 0.67 (volume/volume). Also, a concentration phenomenon is observed during this operation: the tryptophan is eluted to 20 g/L (versus 15 g/L in the feedstock product). More than 99% of the initial tryptophan is recovered in the extract during this step. At each sequence of the SSMB cycle, the amount of NH$_3$ used is 0.59 mol per L of resin, for an injected amount of tryptophan of 1.47 mol/L of resin (i.e. 0.4 mole of NH$_3$ per mole of tryptophan): this demonstrates that the retention mechanism is not ion exchange.

Figure 3:
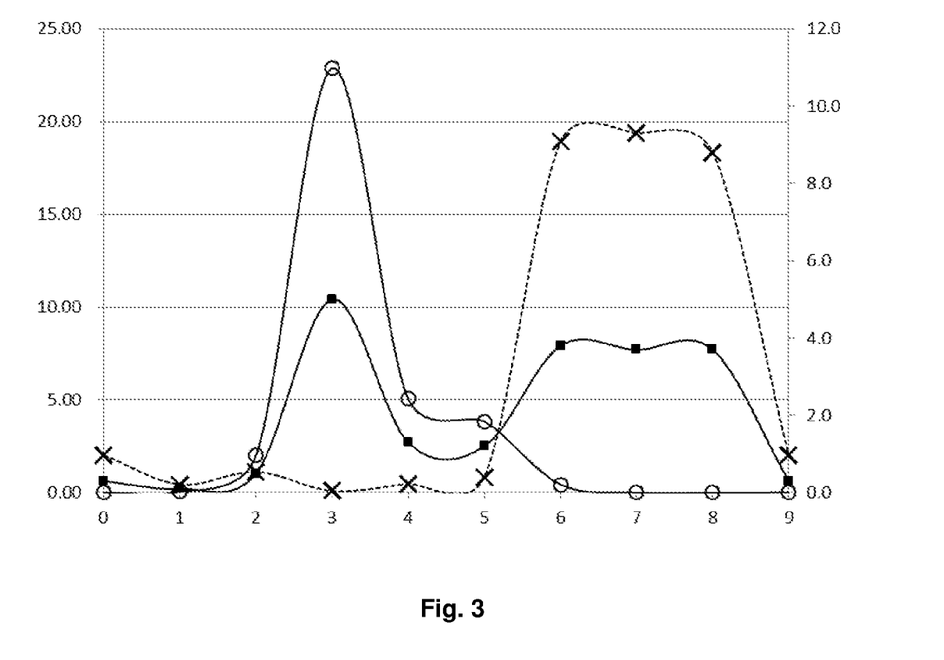
FIG. 3 illustrates the time-dependent change in the tryptophan concentration (in g/L, left-hand scale, symbol O), in conductivity (in mS/cm, left-hand scale, symbol X) and in dry matter amount (in Brix degrees, right-hand scale, symbol ■) on several chromatographic columns (in abscissa, the column number) in a purification system of the SSMB type. The operating conditions are specified in Example 2.

The profile measured in the nine columns, in continuous operation, and during a loop step, is illustrated in FIG. 3. The profiles of tryptophan concentrations, of Brix (representative of the dry material concentration) and of conductivity (representative of the concentration of saline impurities) are represented therein. The separation between the elution zone of tryptophan (zone 1, columns No. 2, 3 and 4) and the zone for collecting the raffinate (zone 3, columns No. 7, 8 and 9) is thus observed.

Example 3

Study of the Retention of Phenylalanine

This example is applied from a fermentation must of phenylalanine, pretreated by adjustment to pH=2, and then by microfiltration on ceramic membranes. The product is treated on an Applexion® XA2014-22 resin, on a 30 mL volume per column=1 BV. The resin is converted beforehand into the NH$_4^+$ form by means of 3% NH$_3$, is rinsed, and then balanced by the passage of NH$_3$ at 2 g/L.

The chromatography feedstock product contains 32.76 g/L of phenylalanine and has a conductivity of 36.8 mS/cm due to the saline concentration of the medium. The feedstock product is injected in excess on the resin, at 4 BV/h: a phenylalanine retention is observed relatively to salts and sugars, and then a leak of the amino acid. Once the outlet concentration is equal to the inlet concentration of amino acid, the injection of the feedstock product is stopped. The elution of phenylalanine is accomplished with an NH$_3$ concentration of 2 g/L, at 4 BV/h.

Figure 4:
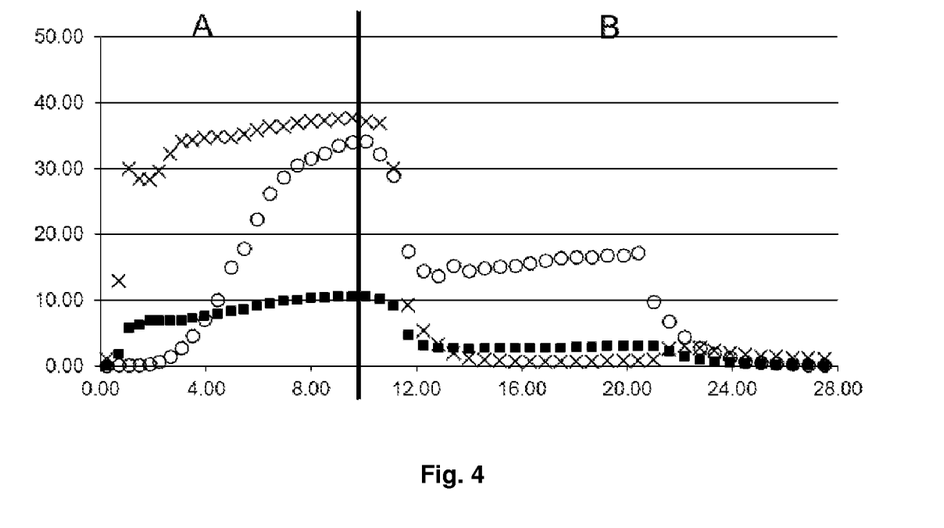
FIG. 4 illustrates the time-dependent change in the phenylalanine concentration (in g/L, symbol O), in conductivity (in mS/cm, symbol X) and in dry matter amount (in Brix degrees, symbol ■) according to the injected volume (in abscissa, in BV) in a chromatographic separation column. The operating conditions are specified in Example 3.

FIG. 4 illustrates the time-dependent change of the concentrations in a point of the system at which the occurrence of the whole of the separation steps is seen, from the beginning of the raffinate elution to the end of rinsing of the extract. Phase A is the injection phase of the initial mixture, phase B is the elution phase with the NH$_3$ solution. This system makes it possible to operate with the following performances:

169 g of phenylalanine treated per liter of resin over a production cycle of 6.75 hours.

a conductivity of about 600 μS/cm during the collection of the phenylalanine extract, corresponding to 98.5% of demineralization.

Example 4

Study of the Retention of Histidine

This example is applied from a 12.98 g/L histidine solution with a conductivity of 17.48 mS/cm and containing 3.9 g/L of sugars. The solution is adjusted beforehand to pH=2.7 by adding H$_2$SO$_4$. The product is treated on an Applexion® XA2014-22 resin, on a 17 mL volume per column (=1 BV). The resin is converted beforehand into the NH$_4^+$ form by means of 3% NH$_3$, is rinsed and then balanced by the passage of NH$_3$ at 2 g/L.

The feedstock product is injected in excess on the resin at 2 BV/h: a phenomenon of retention of histidine is observed and then a leak of amino acid. Once the output concentration is equal to the amino acid inlet concentration, the injection of feedstock product is stopped. The elution of histidine is accomplished with a 2 g/L NH$_3$ concentration at 2 BV/h.

Figure 5:
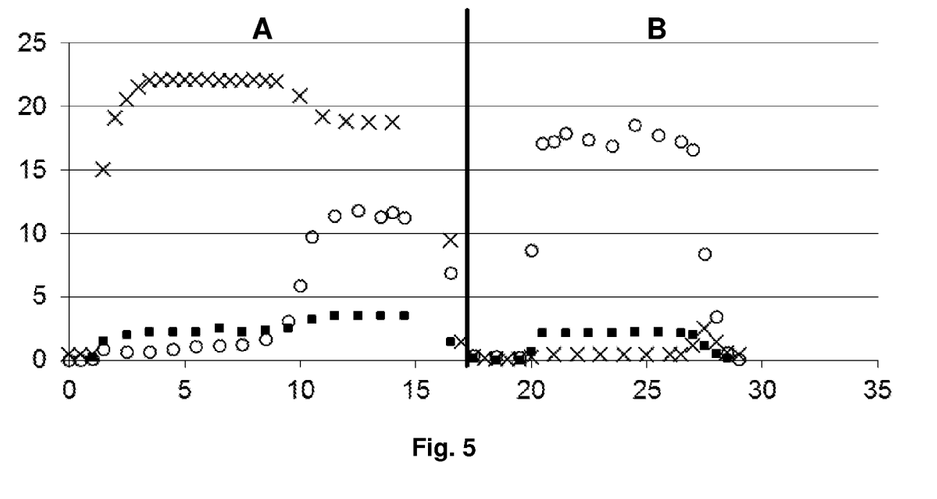
FIG. 5 illustrates the time-dependent change in the histidine concentration (in g/L, symbol O); in conductivity (in mS/cm, symbol X) and in dry matter amount (in Brix degrees, symbol ■) according to the injected volume (in abscissa in BV) in a chromatographic separation column. The operating conditions are specified in Example 4.

FIG. 5 illustrates the time-dependent change in the concentrations in a point of the system at which the occurrence of the whole of the separation steps is seen, from the beginning of the raffinate elution to the end of the rinsing of the extract. Phase A is the injection phase of the initial mixture, phase B is the elution phase with the NH$_3$ solution. This system makes it possible to operate with the following performances:

120 g of histidine treated per liter of resin on a production cycle of 30 hours.

Conductivity of about 220 μS/cm during the collection of the histidine extract, corresponding to 98.8% of demineralization

The invention claimed is:

1. A method for purifying an amino acid from an initial mixture comprising sugars and/or salts, wherein the amino acid comprises an aromatic ring and has an acidity constant Ka, the method comprising:
   (a) a first step of putting the initial mixture into contact with a strong cation resin, at a pH greater than or equal to pKa; and
   (b) a second elution step with an aqueous solution of eluent having a pH greater than the pH of the first step, making it possible to collect a flow enriched in the amino acid and comprising less sugars and/or salts than the initial mixture, wherein the aqueous solution of eluent comprises a base in water and a concentration of the base in the aqueous solution of eluent is from 0.01 g/L to 4 g/L;
   wherein no intermediate rinsing is provided between the first step of putting the initial mixture into contact with a strong cation resin (a) and the second elution step (b) and wherein a ratio of a number of moles of base in the eluent solution used in the second elution step over a number of moles of amino acid in the initial mixture contacted in the first step is less than or equal to 3.

2. The method according to claim 1, wherein the second elution step is an isocratic elution step.

3. The method according to claim 1, wherein the amino acid has a basicity constant Kb, and wherein, during the first step, the pH is less than or equal to pKb−3.

4. The method according to claim 1, wherein the aqueous solution of eluent is a solution of a base in water, the base is selected from the group consisting of soda, potash, and ammonia, or mixtures thereof.

5. The method according to claim 1, wherein the ratio of the number of moles of base in the eluent solution used in the second step over the number of moles of amino acid in the initial mixture contacted in the first step is less than or equal to 2.

6. The method according to claim 1, wherein the amino acid is one of: tryptophan, phenylalanine, tyrosine, or histidine.

7. The method according to claim 1, wherein the strong cation resin is a polystyrene-divinylbenzene copolymer.

8. The method according to claim 1, wherein the strong cation resin has a crosslinking rate from 5 to 12%.

9. The method according to claim 1, wherein the strong cation resin is in a monovalent cationic form.

10. The method according to claim 1, which is applied in a multi-column chromatographic installation, the installation including at most 30 columns.

11. The method according to claim 1, which is applied in a chromatographic installation with a non-static bed comprising one of: (a) a simulated moving bed, (b) an actual moving bed, (c) an improved simulated moving bed, or (d) a sequential simulated moving bed.

12. The method according to claim 1, wherein the initial mixture is obtained at the end of the treatment of a raw mixture, the raw mixture being a fermentative, synthetic or enzymatic must, and the treatment including one or several steps selected from centrifugation, front filtration, crystallization, tangential filtration, microfiltration and ultrafiltration.

13. The method according to claim 1, comprising one or several steps for concentrating the flow enriched in the amino acid, selected from concentration by evaporation with a falling film, concentration by multi-effect evaporation, membrane concentration and notably nanofiltration.

14. The method according to claim 13, wherein, at the end of the concentration step(s), a flow of concentrated amino acid on the one hand and a flow of eluent solution on the other hand are collected, the method comprising the recycling of this flow of eluent solution to the second elution step.

15. The method according to claim 1, wherein the difference between the pH of the eluent solution used in the second step and the pH of the first step is greater than or equal to 2.

16. The method according to claim 1, wherein the first step and the second step provide a chromatographic elution mode where the amino acid is separated from the initial mixture by a delay phenomenon due to affinity of the amino acid with the strong cation resin.

17. A method for purifying an amino acid from an initial mixture comprising sugars and/or salts, wherein the amino acid is selected from the group consisting of: tryptophan, phenylalanine, tyrosine, and combinations thereof and has an acidity constant Ka, the method comprising:
  (a) a first step of putting the initial mixture into contact with a strong cation resin, at a pH greater than or equal to pKa; and
  (b) a second elution step with an aqueous solution of eluent having a pH greater than the pH of the first step, making it possible to collect a flow enriched in the amino acid and comprising less sugars and/or salts than the initial mixture, wherein the aqueous solution of eluent comprises a base in water and a concentration of the base in the aqueous solution of eluent is from 0.01 g/L to 4 g/L;
  wherein no intermediate rinsing is provided between the first step of putting the initial mixture into contact with a strong cation resin (a) and the second elution step (b) and wherein a ratio of a number of moles of base in the eluent solution used in the second elution step over a number of moles of amino acid in the initial mixture contacted in the first step is less than or equal to 3.

* * * * *